United States Patent
Matsui et al.

(10) Patent No.: US 7,881,760 B2
(45) Date of Patent: Feb. 1, 2011

(54) MEASURING STRUCTURE FOR MAGNETO ENCEPHALOGRAPHIC EQUIPMENT WITH A SUPERCONDUCTING MAGNETIC-SHIELD

(75) Inventors: Toshiaki Matsui, Tokyo (JP); Hiroshi Ohta, Tokyo (JP)

(73) Assignee: National Institute of Information and Communications Technology, Tokyo (JP)

( * ) Notice: Subject to any disclaimer, the term of this patent is extended or adjusted under 35 U.S.C. 154(b) by 759 days.

(21) Appl. No.: 11/765,741

(22) Filed: Jun. 20, 2007

(65) Prior Publication Data

US 2008/0108504 A1    May 8, 2008

Related U.S. Application Data

(63) Continuation of application No. PCT/JP2004/019012, filed on Dec. 20, 2004.

(51) Int. Cl.
  *G01R 33/035* (2006.01)
  *A61B 5/05* (2006.01)

(52) U.S. Cl. .................. 505/162; 505/846; 600/408; 600/409; 324/248

(58) Field of Classification Search .......... 505/162, 505/846; 324/248, 262, 301; 600/407–409
  See application file for complete search history.

(56) References Cited

U.S. PATENT DOCUMENTS

| | | | |
|---|---|---|---|
| 5,081,071 A | 1/1992 | Hirschkoff | |
| 5,406,847 A | 4/1995 | Rowe et al. | |
| 5,418,512 A | 5/1995 | Ohta et al. | |
| 6,486,393 B1 | 11/2002 | Matsuba et al. | |
| 6,512,368 B2 | 1/2003 | Tanaka et al. | |

(Continued)

FOREIGN PATENT DOCUMENTS

JP    05-212008    8/1993

(Continued)

OTHER PUBLICATIONS

PCT International Search Report and Written Opinion, International Application No. PCT/JP2004/019012 filed on Dec. 20, 2004, April 4, 2005, (3 pp.).

(Continued)

*Primary Examiner*—Stanley Silverman
*Assistant Examiner*—Kallambella Vijayakumar
(74) *Attorney, Agent, or Firm*—Blakely, Sokoloff, Taylor & Zafman LLP.

(57) ABSTRACT

A magneto-encephalographic equipment superconducting magnetic-shield comprising a vacuum-tight body comprising an outer enclosure wall, a first inner enclosure wall inserted in the outer enclosure wall to define a upper closed space, and a second inner enclosure wall to define a lower open space. The first and second inner enclosure walls are arranged with the bottom of the first inner enclosure wall facing the ceiling of the second inner enclosure wall. A first enclosure of HTSC and a second enclosure of high-permeability material are concentrically arranged in the annular vacuum space defined between the first and second inner enclosure walls and the outer enclosure wall. A head-accommodating area is delimited by the hollow partition between, the bottom of the first inner enclosure wall and the ceiling of the second inner enclosure wall both facing each other, and a plurality of SQUID sensors are arranged in the upper closed space, encircling the head-accommodating area.

4 Claims, 5 Drawing Sheets

U.S. PATENT DOCUMENTS

| | | |
|---|---|---|
| 7,130,675 B2 | 10/2006 | Ewing et al. |
| 7,756,564 B2 | 7/2010 | Matsui et al. |
| 2002/0050815 A1 | 5/2002 | Suzuki et al. |
| 2004/0002645 A1 | 1/2004 | Ewing et al. |
| 2004/0049108 A1 | 3/2004 | Ardenkjaer-Larson et al. |
| 2004/0106863 A1 | 6/2004 | Seki et al. |
| 2004/0254443 A1 | 12/2004 | Gott et al. |
| 2005/0206377 A1 | 9/2005 | Romalis et al. |
| 2005/0272996 A1* | 12/2005 | Matsui et al. ............... 600/409 |

FOREIGN PATENT DOCUMENTS

| | | |
|---|---|---|
| JP | 5-264693 | 10/1993 |
| JP | 07-294613 | 11/1995 |
| JP | 10-313135 | 11/1998 |
| JP | 2002-315729 | 10/2002 |
| JP | 2002-372098 | 12/2002 |
| JP | 2003-010142 | 1/2003 |
| JP | 2001-178695 | 7/2007 |
| WO | WO 2004/066836 | 8/2004 |
| WO | WO 2006/067828 | 6/2006 |

OTHER PUBLICATIONS

Ohta, Hiroshi, Whole-head SQUID Magnetometer in a Superconducting Magnetic Shield, Ceramics 35,(2000), No. 2, pp. 96-102.

Ohta, Hiroshi, et al., Nanometer SNS junctions and their applications to SQUIDS, Physica C 352 (2001), pp. 186-190.

Ohta, Hiroshi, et al., Whole-head SQUID System in a Superconducting Magnetic Shield, Neurology and Clinical Neurophysiology, Nov. 30, 2004:58.

Ohta, Hiroshi, et al., A Whole-head SQUID System in a Superconducting Magnetic Shield, IEEE Trans vol. 17, No. 2, Jun. 2007, pp. 730-733.

Hiroshi Ohta et al., "A 64-Channel Whole-Head SQUID System in a Superconducting Magnetic Shield," Supercond. Sci. Technol. 12 (1999), pp. 762-765, printed in the U.K.

Hiroshi Ohta "Whole-Head-Type SQUID System in a Superconducting Magnetic Shield of High Critical-Temperature Superconductor" Ceramics 35, No. 2, (2000), pp. 96-102.

International Search Report for PCT Counterpart Application No. PCT/JP03/00836, 3 pages. with English translation of the International Search Report for PCT Counterpart Application No. PCT/JP03/00836, 4 pgs. (May 20, 2003).

Patent Cooperation Treaty's Written Opinion for International Application No. PCT/JP03/00836, 6 pgs. with English translation of Patent Cooperation Treaty's Written Opinion for International Application No. PCT/JP03/00836, 5 pgs. (Dec. 2, 2003).

PCT Notification of Transmittal of International Preliminary Examination Report for PCT Counterpart Application No. PCT/JP03/00836, 6 pgs. with English translation of the PCT Notification of Transmittal of International Preliminary Examination Report for PCT Counterpart Application No. PCT/JP03/00836, 5 pgs (Mar. 30, 2004).

\* cited by examiner

MEASURING STRUCTURE FOR MAGNETO ENCEPHALOGRAPHIC EQUIPMENT WITH A SUPERCONDUCTING MAGNETIC-SHIELD

CROSS-REFERENCE TO OTHER APPLICATIONS

This is a continuation of prior PCT Patent Application No. PCT/JP2004/019012, filed on Dec. 20, 2004.

TECHNICAL FIELD

The present invention relates to a magneto encephalographic equipment for measurement of evoked neuro-magnetic field which is produced by nerve current in human brains, and is estimated to be approximately one hundred million times smaller than the magnetic field of the earth.

A SQUID (Superconducting Quantum Interference Device) chip immersed in a liquid helium hath works as a magnetic sensor of high sensitivity at a very low temperature to detect such a weak magnetic field. Thus, observation of the dynamics of neural networks in human brains is enabled. So, the equipment can be used for diagnosis of function of brains (such as memory, learning, attention and other mental activities) and of some brain disorders (attention deficit, hyperactivity disorder, learning disabilities, autism or schizophrenia).

BACKGROUND ART

The present inventor developed an equipment for measurement of neuro-magnetic field above human heads with a SQUID cryogenically cooled by liquid helium and used as a magnetic sensor. The instrument has been practically used.

Referring to FIG. 4, the conventional MagntoEncephalo-Graphic equipment (MEG equipment) in a superconducting magnetic shield comprises a thermal insulator structure of hollow vacuum cylinder 11, a refrigerator unit for circulating Helium gas 12, a cryogenic vessel 13 and a top cover 14. The thermal insulator structure 11 is a double-walled, hollow vacuum cylinder comprising a first enclosure of high critical temperature superconductor 111 and a second enclosure 112 of a high-permeability magnetic material both concentrically arranged in its double cylindrical wall. The refrigerator unit for circulating Helium gas 12 circulates a cooling medium or coolant to cool the first, high critical temperature superconductor enclosure 111 placed in the annular space of the double-wall. The first enclosure 111 has a line cooling pipe wound therearound, and a helium gas is circulated in the cooling pipe to cool the enclosure 111, thereby preventing the surrounding magnetic field from invading the inside of the hollow vacuum cylinder 11. It should be emphasized in FIG. 4 of the conventional MEG equipment that the cryogenic vessel 13 is also a double-walled, hollow vacuum cylinder with a vacuum bottom. In other words, the conventional magnetoencephalographic equipment has two separate hollow vacuum cylinders 11 and 13, which is completely different from the present invention as mentioned later.

The cryogenic vessel 13 is fixedly located in the inside of the hollow vacuum cylinder 11. The top cover 14 is a double-layer enclosure rf-shielded by a metal of good conductivity (electromagnetic wave shield) and shielded magnetically by a magnetic material (magnetic field shield) to fit the top of the hollow vacuum cylinder 11. The lower part of the cryogenic vessel 13 defines a head accommodating area 131 to encircle the head of a test subject. A plurality of SQUID magnetic sensors 15 are mounted on a sensor block 20, which is arranged in the cryogenic vessel 13, spreading over the head accommodating area 131. The cryogenic vessel 13 is filled with a cryogenic coolant or liquid helium The hollow vacuum cylinder 11 stays on the floor with a chair of non-magnetic material 17 arranged in its lower open end. The top cover 14 of magnetic material effectively prevents the electromagnetic wave and the magnetic field of the earth from invading the hollow vacuum cylinder 11. The part of the cap enclosure 14 is removed when one supplies the cryogenic vessel 13 with liquid helium using a transfer tube.

The following documents show the conventional art described above:

Patent Document 1: Patent Application Laid-Open No. H10-313135;
Patent Document 2: International Publication Number WO2004/066836 A1
Non-Patent Document 1: "Whole-Head-Type SQUID System in a Superconducting Magnetic Shield of High Critical-Temperature Superconductor", by Hiroshi Ohta, the magazine, "Ceramics 35" (2000), No. 2, Extra Edition, sub-titled "Brain and Ceramics; Ceramics Useful in Studying Functions of Human Brains, Making the Diagnosis of the Brain Disorders and Carrying out Required Treatments"; and Non-Patent Document 2: "Nanometer SNS Junctions and Their Application to SQUIDs" by Hiroshi Ohta et al the magazine, "PHYSICA C" 352 (2001), pages 186-190.

The hollow vacuum, cylinder 11 and the cryogenic vessel 13 are described below in detail When the first enclosure 111 of high critical-temperature superconductor (bismuth-strontium-calcium-copper-oxide: BSCCO) is cooled down to the vicinity of the liquid nitrogen temperature (103K or below), no magnetic flux is allowed to invade the inside of the hollow vacuum cylinder 11 from the exterior. Before the temperature of the first enclosure 111 is lowered, there already stays a significant amount of magnetic flux due to the magnetic field of the earth in the inside of the hollow vacuum cylinder 11. The magnetic flux due to the magnetic field of the earth is trapped in the first enclosure 111 when the temperature is lowered below the critical temperature of BSCCO. The axial or radial movement of the cryogenic vessel 13 will change the relative displacement between the component of the trapped magnetic field and the pick-up coils of the SQUID magnetic sensors generating noise outputs in the measurement. The way to eliminate such noise outputs is to: keep the relative displacement between the hollow vacuum cylinder 11 and the cryogenic vessel 13 constant; and mechanically isolate the hollow vacuum cylinder 11 from the floor on which the magneto encephalographic equipment stands, thereby blocking any mechanical vibrations which otherwise would be transferred to the hollow vacuum cylinder 11 from the floor. Thus, the magneto encephalographic equipment is guaranteed to be free of change of relative displacement between the cryogenic vessel 13 and the first, enclosure 111 in the hollow vacuum cylinder 11 (see Patent Document 2). Specifically pillow blocks are used to fill the space between the inner wall of the hollow vacuum cylinder 11 and the outer wall of the cryogenic vessel 13, and the hollow vacuum cylinder 11 is fixed to the floor via a vibration-isolation support, which comprises mechanical dumpers and an active vibration isolation unit. Such vibration isolation method is quite useful in effectively removing noises if any during the measurement of the neuro-magnetic field and improving Signal-to-Noise ratio of magnetoencephalography data.

Our goal is to make a maintenance-free operation of a MEG equipment using an available power of a commercial closed-cycle helium refrigerator. Our preliminary experiment with a commercial closed-cycle helium refrigerator teaches that the heat flow through the vacuum thermal insulation between the two walls of the double-layer cryogenic vessel 13 beats the available cooling power of a commercial closed-cycle helium refrigerator and that the level of the liquid helium inside the cryogenic vessel decreases gradually.

Now, what remains unsolved is to minimize the heat flow into the cryogenic vessel 13 so that the available cooling power of a commercial closed-cycle helium refrigerator can manage to keep the level of liquid helium constant in the cryogenic vessel 13.

It is practically impossible from both points of design's view and maintenances view that the cooling power of a commercial helium refrigerator beats the heat flow into the cryogenic vessel 13 in the conventional configuration as shown in FIG. 4.

Details are following. The cryogenic vessel 13 contains approximately 40 liters of liquid helium (−270° C.), which constantly evaporates and changes into a helium gas, discharging into the atmosphere while the measuring equipment works. Approximately 20 liters of liquid helium evaporates every day, and therefore, the equipment needs to be supplied with 20 liters of liquid helium every day. The running cost due to liquid helium consumption is approximately ten million yen per year. The cryogenic liquid must be handled with considerable care and otherwise it might boil explosively, and therefore, some experts capable of handling such cryogenic liquid need to be retained. In the hope of solving these maintenance problems it is proposed that helium gas is used as a substitute for the liquid, helium; the gas can be pumped and circulated from the cryogenic refrigerator. If the conventional configuration as shown in FIG. 4 is not changed and the heat flow into the cryogenic vessel 13 is not reduced, then the required capacity or cooling power of the closed-cycle helium refrigerator must be huge and impractical. As a matter of fact a refrigerator whose capacity is large enough to provide such a cooling capacity is too large to be produced, installed and operated. The helium gas circulating refrigerator system is barely able to meet the cooling of the magnetic shield enclosure 111 at a temperature of liquid nitrogen temperature (−200° C.) much higher than the liquid helium temperature— the temperature at which the cryogenic vessel 13 needs to be cooled. Therefore there is no other way than managing to reduce the heat flow into the cryogenic vessel 13 some way. In this connection the liquid and gas cooling modes are being selectively used at present: the cryogenic vessel 13 is liquid-cooled while being constantly supplied with as much liquid helium as evaporated whereas the first enclosure 111 of high critical temperature superconductor located within the double wall is gas-cooled by circulating helium gas.

DISCLOSURE OF THE INVENTION

What is aimed at by the present invention is to solve the above described problems for maintenance in the superconducting magnetic-shielded magneto encephalographic equipment in consideration of the actual cooling capability of the refrigerator while the equipment is guaranteed to be free from degradation of experimental data by noise due to mechanical vibration. One object of the present invention, therefore, is to provide a new way whereby the available cooling capacity of a commercial helium refrigerator can heat the heat flow into the cryogenic vessel 13 and to get a maintenance-free magneto encephalographic equipment in a superconducting magnetic shield.

Referring to FIG. 4 again, there is an annular space between the cryogenic vessel 13 and the hollow vacuum cylinder 11, and the temperature of the annular space is at room temperature. The present inventor found the new way to reduce the heat flow into the cryogenic vessel 13 as indicated by arrows to increase evaporation of the liquid helium. The present invention is the new way to reduce the heat flow into the cryogenic vessel 13. To prevent the invasion of the heat from the exterior it suffices that the cryogenic vessel 13 and the hollow vacuum cylinder 11 be connected as an integrated whole to remove such annular space. As a matter of fact, the integral structure effectively halves the consumption of liquid helium. Still advantageously, the integral structure makes it possible to minimize the relative displacement between the cryogenic vessel 13 and the hollow vacuum cylinder 11, and hence reduce noise due to vibration, thus excluding the necessity of providing the magneto encephalographic equipment with the vibration isolation means.

The magneto encephalographic equipment may be so redesigned that: adiabatic expansion of helium gas provides as much liquid helium as required for compensating evaporation; or otherwise, the so liquefied helium gas (liquid helium) is made to be put in indirect contact with the SQUID magnetic sensors for cooling them by thermal conduction. In this case the integral structure effectively prevents heat from flowing into the cryogenic vessel 13, and therefore, the load on the helium refrigerator is reduced to such an extent that the required cooling capacity is of practically attainable largeness. Thus, as is the case with the first enclosure of high critical temperature superconductor to prevent invasion of exterior magnetic field, the SQUID magnetic sensor can be cooled by helium gas rather than liquid helium, which is difficult to work with. Advantageously, this makes it possible to operate the neuro-magnetic field measuring equipment only with the electric energy as much as required for operating the helium gas refrigerator.

A measuring structure for a magneto encephalographic equipment with a superconducting magnetic shield according to the present invention comprises:

an vacuum-tight structure comprising: an outer enclosure wall; a first inner enclosure wall inserted in the outer enclosure wall to define an upper closed space; and a second inner enclosure wall to define a lower open space, the first and second inner enclosure walls being arranged with the bottom of the first inner enclosure wall facing the ceiling of the second inner enclosure wall, thereby forming the vacuum-tight space by the first and second inner enclosure walls in the outer enclosure wall;

a first enclosure of high critical temperature superconductor;

a second enclosure of high permeability material, the first and second enclosures being arranged in the annular vacuum space defined between the first, and second inner enclosure walls and the outer enclosure wall; and a plurality of SQUID sensors arranged in the upper closed space, encircling the head accommodating area, which is delimited by the hollow partition between the bottom of the first inner enclosure wall and the ceiling of the second inner enclosure wall; the SQUID sensors being adapted to be cooled by the coolant in the upper closed space whereas the first inner enclosure of high critical temperature superconductor being adapted to be cooled by the coolant in the annular vacuum space.

The integral cylindrical structure effectively prevents the heat from flowing into the upper closed space sideways, remarkably reducing consumption of the coolant, and at the same time, the integral structure effectively eliminates the noises caused by vibration, accordingly improving signal-to-noise ratio of experimental data. The magneto encephalographic equipment with a superconducting magnetic shield can be operated by using a cryogenic refrigerator of practically obtainable cooling capacity.

The coolant contained in the upper closed space is liquid helium whereas the coolant to cool the first enclosure of high critical temperature superconductor is helium gas. The consumption of the liquid helium during operation is, in fact, halved.

An adiabatic expansion compartment may be placed in the upper closed space. The coolant for the upper closed space is liquid helium whereas the coolant which the adiabatic expansion compartment is supplied with is cooled helium gas, which is liquefied in the adiabatic expansion compartment, and is fed to the upper closed space in the form of drops, thus making up for the consumption of liquid helium. The first enclosure of high critical temperature superconductor may be cooled by the helium gas from the same cryogenic refrigerator as used for the adiabatic expansion compartment, or from another cryogenic refrigerator.

Since the consumption of liquid helium is compensated, this arrangement enables the magneto encephalographic equipment with a superconducting magnetic-shield to run without intermission.

An adiabatic expansion compartment may be placed in the upper closed space. The coolant for the upper closed space is liquid helium, whereas the coolant which the adiabatic expansion compartment is supplied with is cooled helium gas, which is liquefied in the adiabatic expansion compartment to indirectly cool the SQUID magnetic sensors by thermal conduction. The coolant to cool the first enclosure of high critical temperature superconductor is cooled helium gas.

With this arrangement the SQUID magnetic sensors and the first enclosure of high critical temperature superconductor for magnetic shield can be cooled only by operating the helium refrigerator. Thus, the liquid nitrogen or liquid helium which is difficult to handle or work with is not required, and the magneto encephalographic equipment in a superconducting magnetic-shield continues to work only with electric energy with which the refrigerator is supplied. Advantageously the refrigerator can be supplied with electricity from the commercial electric source (100 volts), and is small in size. The measuring structure makes the sensors insensitive to vibrations, and therefore, the magneto encephalographic equipment can be carried by a vehicle for itinerant medical service.

BEST MODE FOR CARRYING OUT THE INVENTION

Referring to FIG. 1, a cylindrical measuring structure 1 for a magneto encephalographic equipment with a superconducting magnetic-shield according to the present invention comprises an outer enclosure wall 114, a first inner enclosure wall 115 inserted in the outer enclosure wall 114 to define an upper closed space S1 and a second inner enclosure wall 116 to define a lower open space; S2. As shown in the drawing, the first and second inner enclosure walls 115 and 116 are concentrically arranged with the bottom of the first inner enclosure wall 115 facing the ceiling of the second inner enclosure wall 116.

The outer wall 114, the first inner enclosure wall 115 and the second inner enclosure wall 116 together form an annular space in which the first enclosure 111 of high critical temperature superconductor and the second enclosure wall 116 of high permeability material are concentrically arranged, and the annular space is evacuated to provide a vacuum compartment. The so formed vacuum-tight structure provides a thermal insulation from the exterior.

A head-accommodating area 131 is delimited by a concave depression 131 made at the center of the hollow partition between the bottom of the first inner enclosure wall 115 and the ceiling of the second inner enclosure wall 116, and a plurality of SQUID sensors 15 are arranged in the upper closed space S1, encircling the head-accommodating area 131. The SQUID sensors 15 are supported by a sensor head 20.

In the upper space S1 the SQUID magnetic sensors 15 are cooled in the liquid helium hath H whereas the vacuum annular space is cooled by cooled helium gas, which is fed from the closed-cycle helium refrigerator via a coiled pipe (not shown) wound around the first enclosure 111 of high critical temperature superconductor. A test subject sits on the non-metal chair 17 with his or her head put in the concave head-accommodating area 131.

Referring to FIGS. 5A and 5B, how the magneto encephalographic equipment of the present invention is different from the prior art apparatus is described below. FIGS. 5A and 5B illustrate the measuring structures for the magneto encephalographic equipment of FIG. 1 and for the prior art apparatus of FIG. 4, respectively. As seen from FIG. 5A, the measuring structure according to the present invention comprises a vacuum partition V1 defined by the outer enclosure wall 114, the first inner enclosure wall 115 and the second inner enclosure wall 116. In contrast, in the prior art measuring structure of FIG. 5B the cylindrical vacuum thermal insulation body 11 is separated from the cryogenic vessel 13. Particularly the vacuum partition V2 of the cylindrical vacuum thermal insulation body 11 is separated from the vacuum partition V3 of the cryogenic vessel 13. Only for the sake of illustration FIGS. 5A and 5B show the hermetically sealed vacuum walls as being open at their ends, hut these vacuum walls are hermetically sealed for example, with "O"-ring seals.

Referring to FIG. 2, a measuring structure 1 according to a second embodiment of the present invention is similar to the first embodiment of the present invention (FIG. 1) except for an adiabatic expansion compartment 117 placed in the upper closed space S1, which is defined by the first inner enclosure wall 115. The coolant for the upper closed space is liquid helium H whereas the coolant for the adiabatic expansion compartment 117 is cooled helium gas, which is liquefied in the adiabatic expansion compartment 117. The so converted liquid helium is fed to the upper closed space in the form of drops to make up for the evaporation of liquid helium during the operation. The helium gas to cool the first enclosure 111 of high critical temperature superconductor is supplied from the helium refrigerator 12 whereas the helium gas to the adiabatic expansion compartment 117 is supplied from the helium refrigerator 214. Thus, the magneto encephalographic equipment can continue to work without intermission, which otherwise would be required for making up for the evaporated coolant with a transfer-tube of liquid helium from a container of liquid helium.

Referring to FIG. 3, a measuring structure according to the third embodiment of the present invention is similar to the second embodiment of FIG. 2 except for a heat conduction body 118 connecting the sensor head 20 of the SQUID magnetic sensors 15 to the adiabatic expansion compartment 117. The heat conduction body 118 is made of a metal of good thermal conductivity, and the sensor head 20 of the SQUID magnetic sensors 15 is put in indirect contact with the liquefied helium gas (liquid helium) in the adiabatic expansion compartment 117 via the heat conduction body 118, thereby absorbing heat from the SQUID magnetic sensors 15 by thermal conduction. The upper closed space S1 is evacuated or otherwise, filled with low pressure of helium gas, but not loaded with liquid helium. With this arrangement the helium gas (20K) fed to the adiabatic expansion compartment 117 is converted into the liquid helium (4.3K) in the adiabatic expansion compartment 117 to indirectly cool the SQUID magnetic sensors by thermal conduction. The cooled helium gas is supplied from the closed-cycle helium refrigerator 12 to the first enclosure 111 whereas the helium gas is supplied from the closed-cycle helium refrigerator 214 to the adiabatic expansion compartment 117. Thus, the magneto encephalographic equipment can continue to work only with the electric energy as much as required for operating these refrigerators.

INDUSTRIAL APPLICABILITY

The measuring structure according to the present invention makes it possible to practically use the magneto encephalographic equipment. Particularly the measuring structures according to the second and third embodiments of the present invention make it possible to continuously operate the magneto encephalographic equipment simply by operating associated closed-cycle helium refrigerators in the circumstances in which the commercial power supply is available. As for the third embodiment using only helium gas as a coolant, the magneto encephalographic equipment can be carried by a vehicle, permitting it to work without unburdening the MEG equipment. Thus, the horizon of the itinerant medical service is expanded to encompass diagnosis of the function of the brain (such as memory, learning, attention and other mental acts) and of some brain disorders (attention deficit, hyperactivity disorder, learning disabilities, autism or schizophrenia) including a mobile clinic for mental health care.

Figure 1:
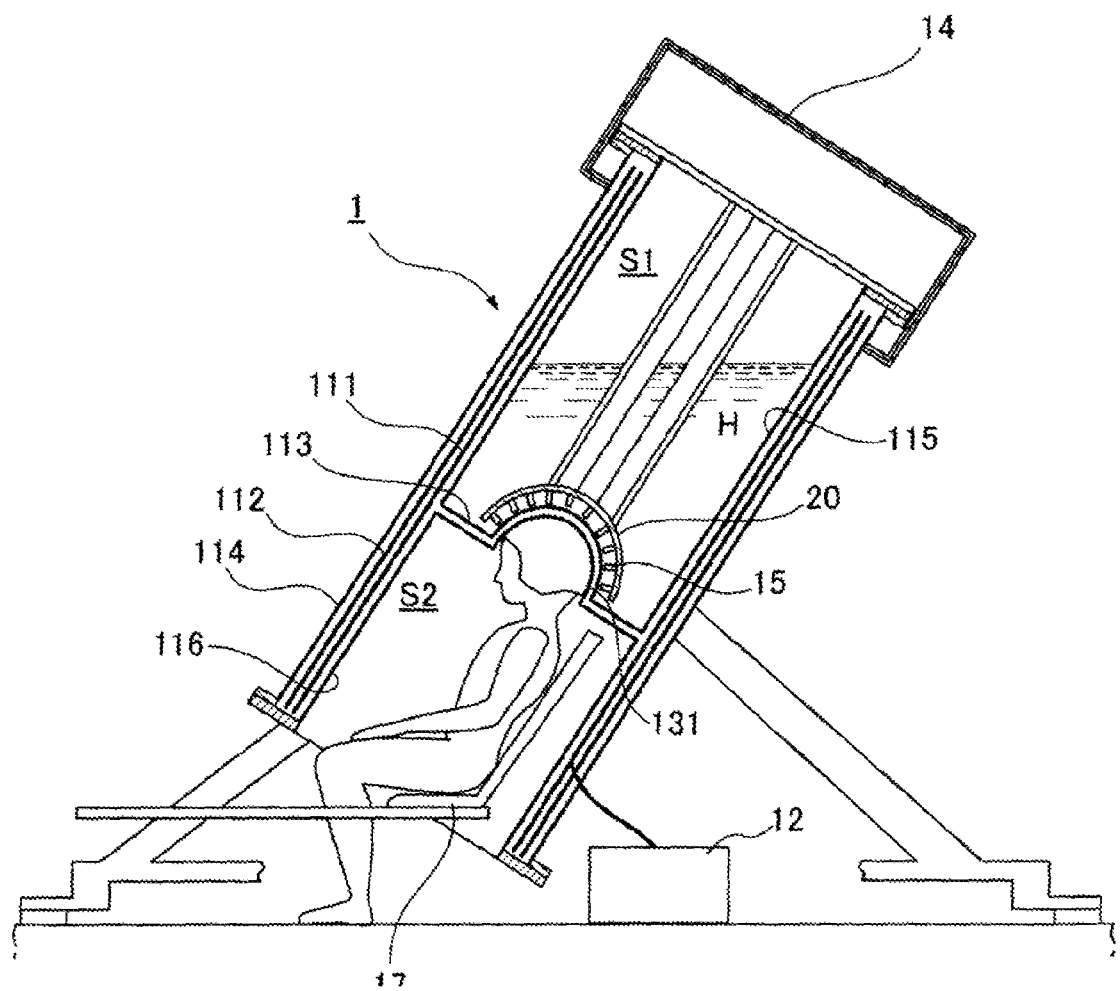
FIG. 1 illustrates a magneto encephalographic equipment using a measuring structure according to the first embodiment of the present invention.
Figure 2:
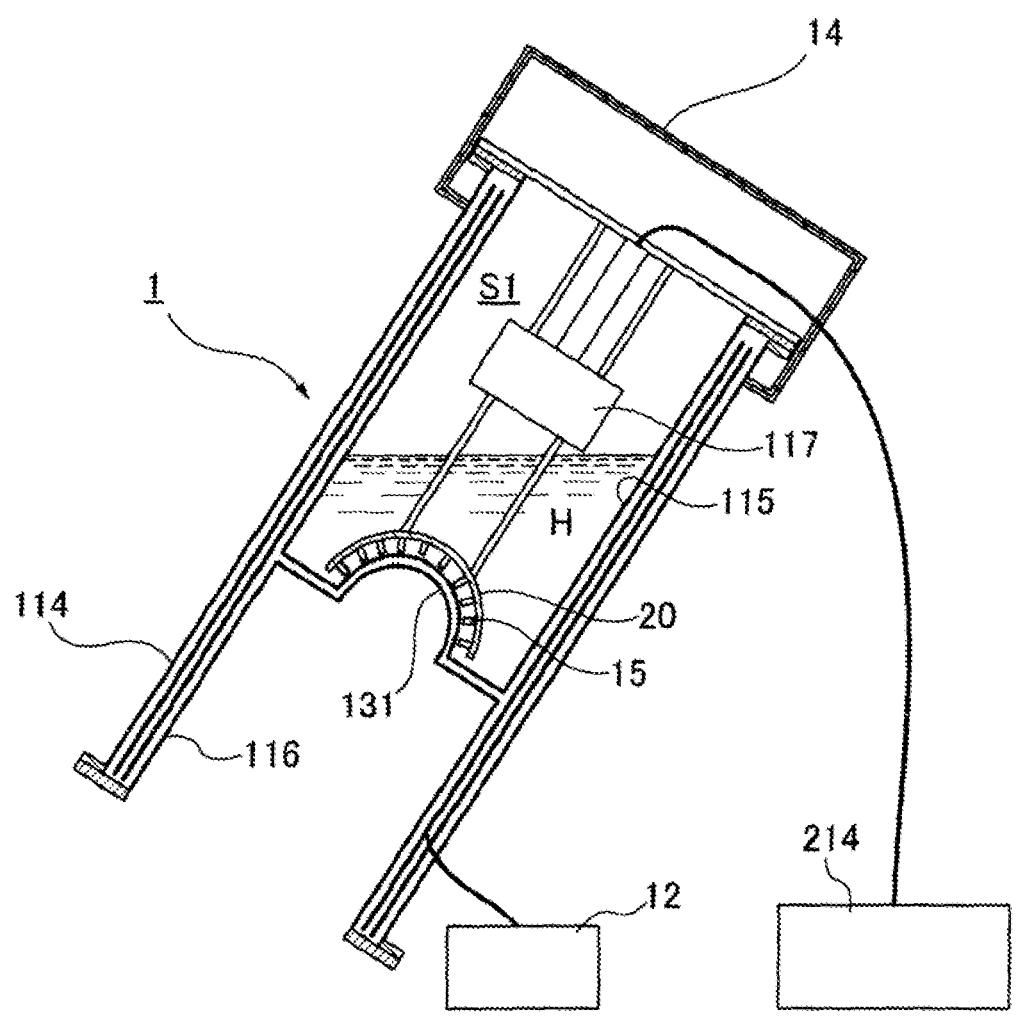
FIG. 2 illustrates a measuring structure according to the second embodiment of the present invention.
Figure 3:
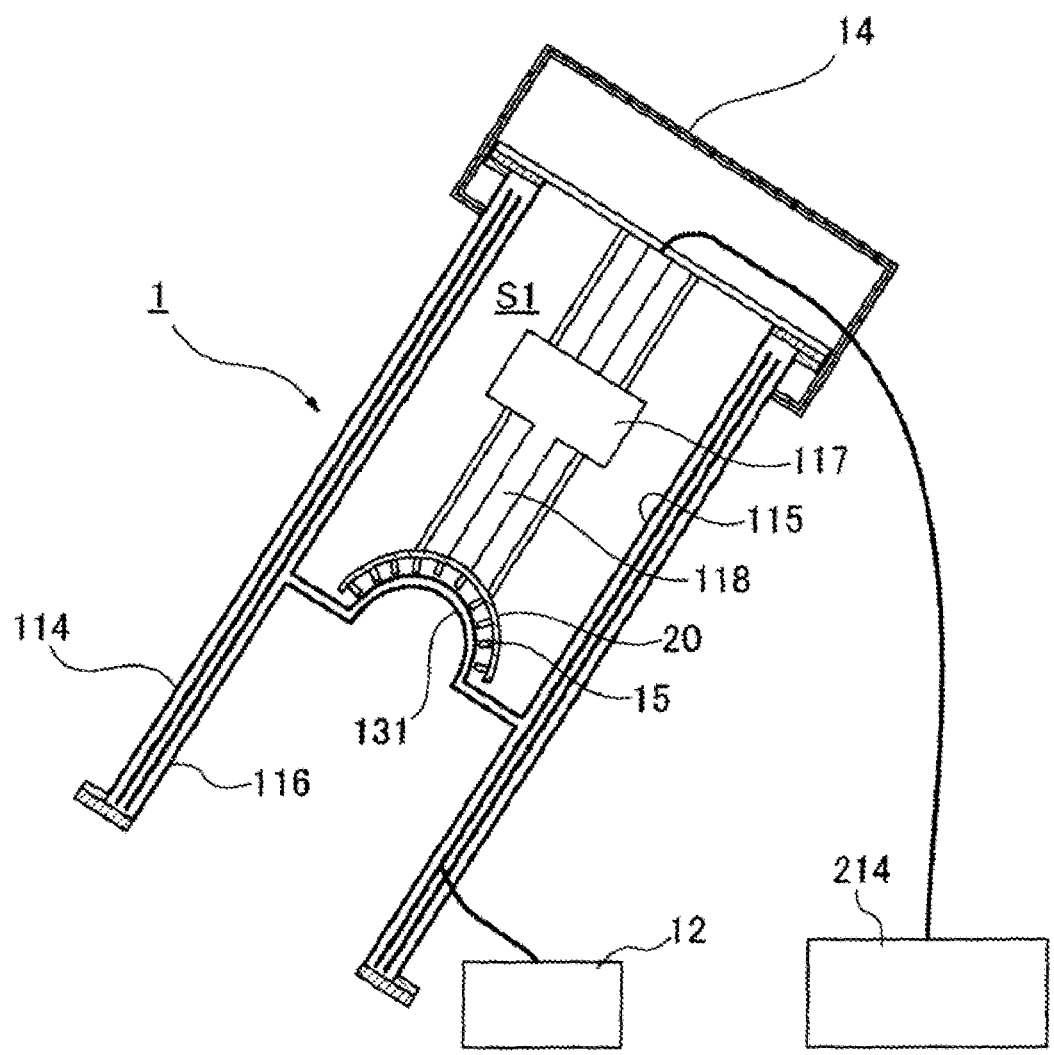
FIG. 3 illustrates a measuring structure according to the third embodiment of the present invention.
Figure 4:
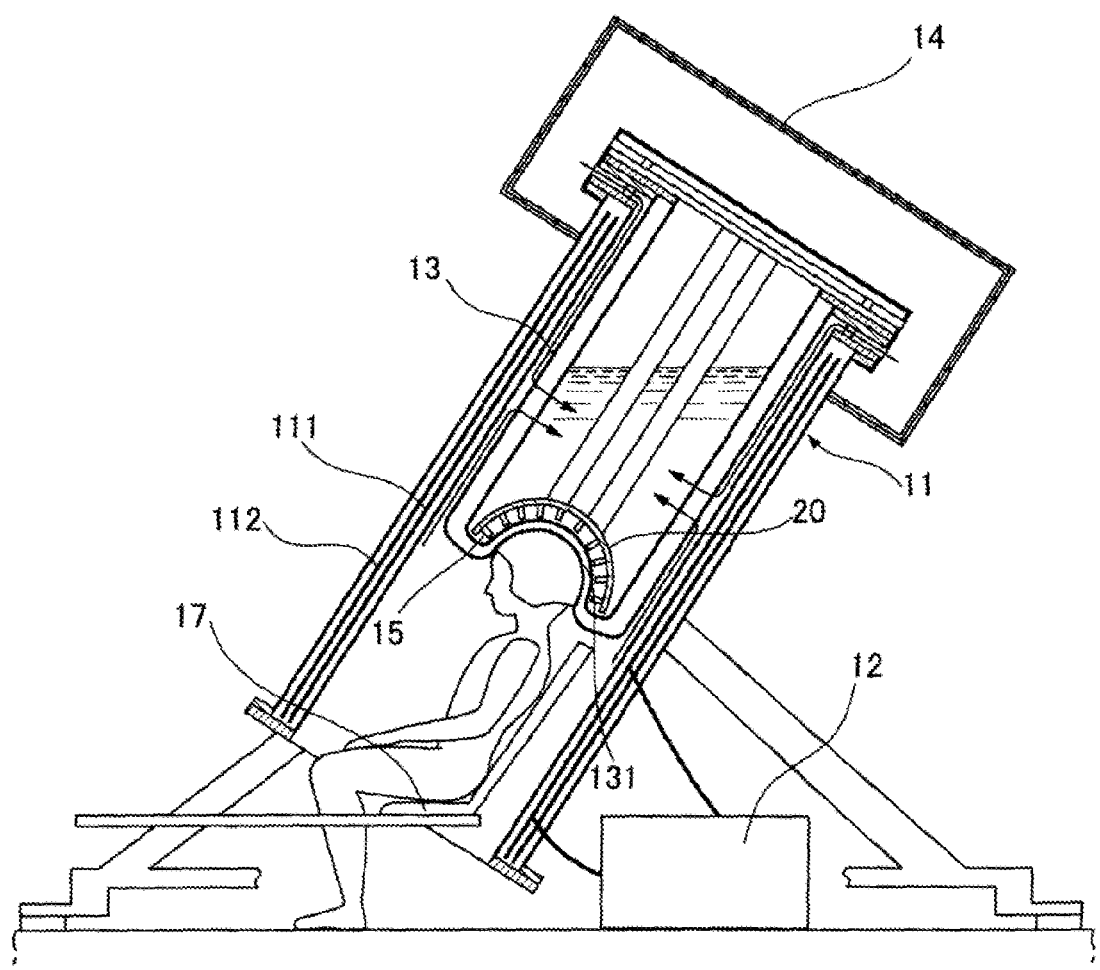
FIG. 4 illustrates a conventional magneto encephalographic equipment.
Figure 5A:
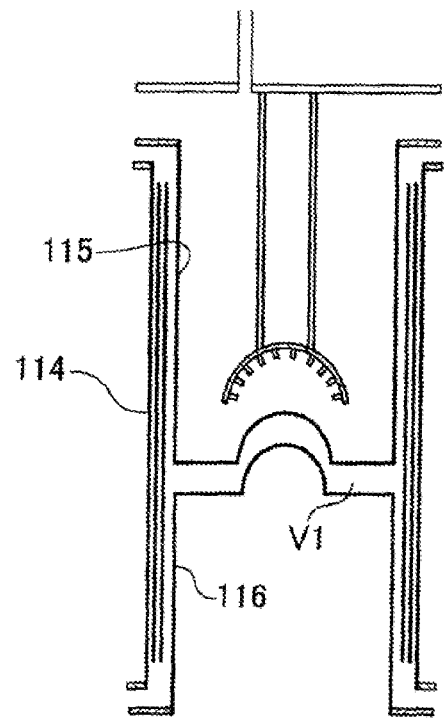
FIG. 5A illustrates the structure of the magneto encephalographic equipment according to the present invention.
Figure 5B:
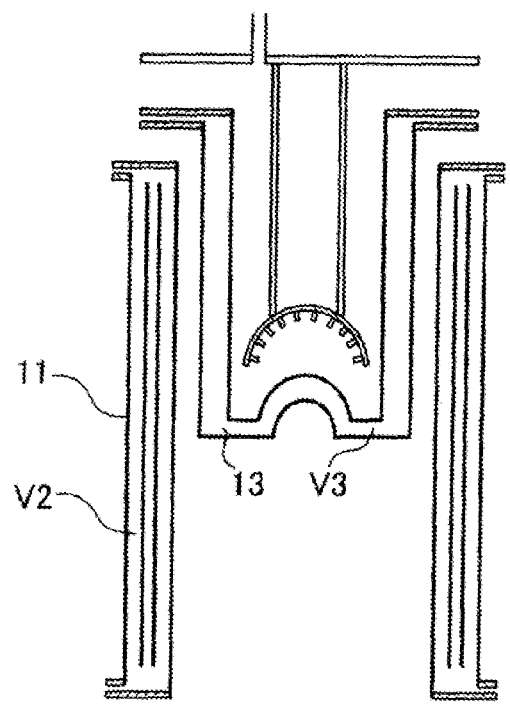
FIG. 5B illustrates the prior art structure of the magneto encephalographic equipment.

The invention claimed is:

1. A measuring structure for a magneto encephalographic equipment in a superconducting magnetic-shield comprising:
    an vacuum-tight structure comprising:
        an outer enclosure wall;
        a first inner enclosure wall inserted in the outer enclosure wall to define an upper closed space; and
        a second inner enclosure wall to define a lower open space, the first and second inner enclosure walls being arranged with the bottom of the first inner enclosure wall facing the ceiling of the second inner enclosure wall, thereby forming the vacuum-tight space by the first inner enclosure wall, the second inner enclosure wall and the outer enclosure wall;
    a first enclosure of high critical temperature superconductor;
    a second enclosure of high permeability material, the first and second enclosures being arranged in the annular vacuum space defined between the first and second inner enclosure walls and the outer enclosure wall; and
    a plurality of SQUID sensors arranged in the upper closed space, encircling the head-accommodating area, which is delimited by the hollow partition between the bottom of the first inner enclosure wall and the ceiling of the second inner enclosure wall; the SQUID sensors being adapted to be cooled by the coolant in the upper closed space whereas the first inner enclosure of high critical temperature superconductor being adapted to be cooled by the coolant in the annular vacuum space.

2. A measuring structure for a magneto encephalographic equipment in a superconducting magnetic-shield according to claim 1 wherein the cooling medium contained in the upper closed space is liquid helium whereas the cooling medium to cool the first enclosure of high critical temperature superconductor is cooled helium gas.

3. A measuring structure for a magneto encephalographic equipment in a superconducting magnetic-shield according to claim 1 wherein it further comprises an adiabatic expansion compartment, the cooling medium contained in the upper closed space being liquid helium whereas the cooling medium fed to the adiabatic expansion compartment being cooled helium gas, which is converted into the liquid helium by adiabatic expansion, and is fed to the upper closed space to make up for evaporation, whereas the cooling medium to cool the first enclosure of high critical temperature superconductor being cooled helium gas.

4. A measuring structure for a magneto encephalographic equipment in a superconducting magnetic-shield according to claim 1 wherein it further comprises an adiabatic expansion compartment, the cooling medium fed to the adiabatic expansion compartment being cooled helium gas, which is converted into the liquid helium by adiabatic expansion to indirectly cool the SQUID magnetic sensors via an associated thermal conduction body, the cooling medium to cool the first enclosure of high critical temperature superconductor being cooled helium gas.

* * * * *